United States Patent
Wickline et al.

(10) Patent No.: US 8,353,838 B2
(45) Date of Patent: Jan. 15, 2013

(54) ULTRASONIC PROBE VOLUME COMPENSATION SYSTEM

(75) Inventors: Kevin Wickline, Yeagertown, PA (US); Jeffrey Hart, Reedsville, PA (US); Alan Hornberger, McAlisterville, PA (US); Mark Harpster, Burnham, PA (US); Charles Cruikshank, Belleville, PA (US); David Becker, Lewistown, PA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1043 days.

(21) Appl. No.: 10/599,312

(22) PCT Filed: Mar. 22, 2005
(Under 37 CFR 1.47)

(86) PCT No.: PCT/IB2005/050985
§ 371 (c)(1),
(2), (4) Date: Sep. 25, 2006

(87) PCT Pub. No.: WO2005/094690
PCT Pub. Date: Oct. 13, 2005

(65) Prior Publication Data
US 2007/0293761 A1     Dec. 20, 2007

Related U.S. Application Data

(60) Provisional application No. 60/559,379, filed on Apr. 2, 2004, provisional application No. 60/559,321, filed on Apr. 2, 2004, provisional application No. 60/559,390, filed on Apr. 2, 2004.

(51) Int. Cl.
*A61B 8/12*      (2006.01)
*A61B 8/14*      (2006.01)

(52) U.S. Cl. ........ 600/459; 600/437; 600/443; 600/462; 600/463; 600/466

(58) Field of Classification Search ................. 600/459, 600/463, 437–449, 462, 466
See application file for complete search history.

(56) References Cited

U.S. PATENT DOCUMENTS

| | | | |
|---|---|---|---|
| 4,517,840 A | | 5/1985 | Thompson et al. |
| 4,784,148 A | | 11/1988 | Dow et al. |
| 5,117,831 A | * | 6/1992 | Jang et al. .................... 600/463 |
| 5,178,150 A | * | 1/1993 | Silverstein et al. ........... 600/463 |
| 5,226,422 A | | 7/1993 | McKeighen et al. |
| 5,738,901 A | * | 4/1998 | Wang et al. ..................... 427/2.3 |
| 5,830,182 A | * | 11/1998 | Wang et al. ................. 604/96.01 |
| 5,882,302 A | * | 3/1999 | Driscoll et al. ............... 600/371 |

(Continued)

FOREIGN PATENT DOCUMENTS

EP     0089131 A     9/1983

(Continued)

*Primary Examiner* — Tse Chen
*Assistant Examiner* — Vani Gupta

(57) ABSTRACT

An ultrasound probe includes a transducer which is pivotally mounted inside a fluid chamber for scanning a region outside the probe as the transducer is oscillated. A volume compensation balloon is attached to the fluid chamber and is partially filled with acoustic fluid at nominal (room) temperatures. The balloon is made of a high performance thermoplastic which enables the balloon to have a very thin wall. The thin wall is highly compliant as the volume of the fluid inside the balloon changes, and remains so at low temperatures of transport and use. The thin wall exhibits a low permeability to the acoustic fluid. The balloon is formed of a non elastic material and exhibits good thermal stability and high burst strength.

18 Claims, 3 Drawing Sheets

U.S. PATENT DOCUMENTS

| | | | |
|---|---|---|---|
| 6,592,526 B1 * | 7/2003 | Lenker | 600/463 |
| 7,081,113 B2 * | 7/2006 | Sutton | 606/27 |
| 7,479,128 B1 * | 1/2009 | Lenz | 604/265 |
| 2003/0083653 A1 * | 5/2003 | Maguire et al. | 606/41 |

FOREIGN PATENT DOCUMENTS

| | | |
|---|---|---|
| JP | 20050141428 A | 5/2004 |

* cited by examiner

ULTRASONIC PROBE VOLUME COMPENSATION SYSTEM

CROSS REFERENCE TO RELATED APPLICATION

This application claims the benefit of U.S. provisional application Ser. No. 60/559,379 filed Apr. 02, 2004, which is incorporated herein.

This invention relates to medical diagnostic imaging systems and, in particular, to fluid filled probes for three dimensional imaging with ultrasonic diagnostic imaging systems.

Ultrasonic probes always benefit from a good acoustic path between the transducer and the patient's body. With static probes in which the transducer does not move, the transducer is covered with an acoustic window that is highly transmissive of ultrasound, generally a rubber-like material. The acoustic path to the body is completed with an acoustic gel between the acoustic window and the skin of the patient, which prevents air and air bubbles from obstructing or interfering with the passage of acoustic energy into and out of the body.

Mechanical probes have been in use for many years in which the transducer is oscillated to sweep a beam of ultrasound through the body for imaging. The first mechanical probes employed single element transducers which were oscillated in a fluid bath that provided acoustic coupling from the transducer element to the acoustic window. The acoustic gel would then couple the ultrasound energy between the acoustic window and the body. This same approach was used with oscillating annular array transducers, in which the annular array was electronically focused as its beam was swept through an image plane of the patient.

In recent years the use of mechanical single element probes has declined as static array probes with electronic beam steering have replaced them. But with the recent advent of live three dimensional ultrasonic imaging, mechanical probes have begun to appear which oscillate an array of transducers that electronically steers beams as the array is moved. The array transducer can be electronically controlled to steer beams in the azimuth direction as the mechanical oscillation moves the array in the elevation direction, thereby transmitting and acquiring ultrasonic energy from a volumetric region rather than just a plane. In essence, the array electronically scans a plane and the plane is mechanically swept through the volume being imaged. These three dimensional mechanical array probes, like their single element ancestors, need a means for coupling ultrasonic energy from the moving transducer to the acoustic window. Like their predecessors, a fluid bath is the most common and convenient coupling means.

With fluid bath probes come the familiar challenges which fluids present. Fluid-filled probes can leak and can develop air bubbles in the fluid which can interfere with the acoustic path. These problems are often the result of expansion and contraction of the fluid and probe components with changes in temperature and pressure. A probe shipped by airplane can be subject to low pressures and temperatures during transit, whereas a probe left in an automobile in the sun can be subject to high temperatures. Accordingly it is desirable to provide a means for accommodating such expansion and contraction within the probe itself so as to prevent the development of fluid leakage and air bubbles in the acoustic path of the probe.

In accordance with the principles of the present invention a fluid-filled ultrasound probe with a moving transducer is described which includes a volume compensation system that accommodates changes in fluid volume with changes in temperature or pressure. The volume compensation system includes a thin-walled balloon made of a high performance thermoplastic material which is coupled to the fluid chamber for the transducer. At nominal temperatures and pressures the balloon is partially collapsed so that it will respond to increases or decreases in pressure or temperature by collapsing or expanding without reaching its expansion limit. The thermoplastic material enables the balloon wall to be very thin which offers little resistance to the filling and emptying of the balloon with changes in fluid temperature or pressure. In accordance with a further aspect of the present invention, the thin-walled balloon has a low permeability to the fluid which fills the fluid chamber of the probe. A desirable balloon material should also exhibit high integrity in terms of tear strength, burst strength, and puncture strength.

Figure 1:
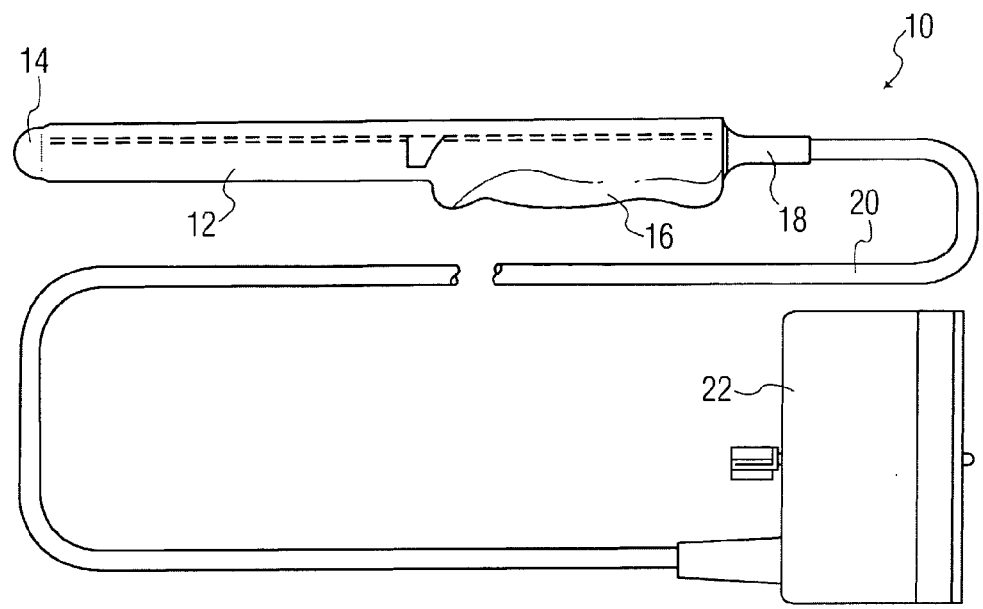
FIG. 1 illustrates a typical intracavity ultrasound probe of the prior art.

Referring first to FIG. 1, a typical IVT intracavity ultrasound probe of the prior art is shown. This probe includes a shaft portion 12 of about 6.6 inches (16.7 cm) in length and one inch (2.54 cm) in diameter which is inserted into a body cavity during use. The ultrasound transducer is located in the distal tip 14 of the shaft. In this probe the transducer is a static curved array transducer which is able to scan a planar sector around the tip of the probe. The probe is grasped and manipulated by a handle 16 during use. At the end of the handle is a strain relief 18 for a cable 20 which extends about 3-7 feet and terminates at a connector 22 which couples the probe to an ultrasound system. A typical two dimensional imaging IVT probe such as the one shown in FIG. 1 may have a shaft and handle which is 12 inches in length and weigh about 48 ounces (150 grams) including the cable 20 and the connector 22.

Figure 2:
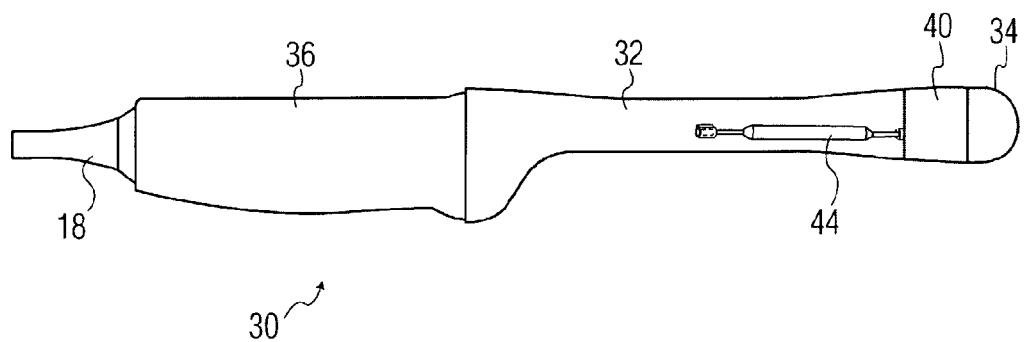
FIG. 2 illustrates a partially cut-away side view of an intracavity probe for three dimensional imaging of the present invention.
Figure 3:
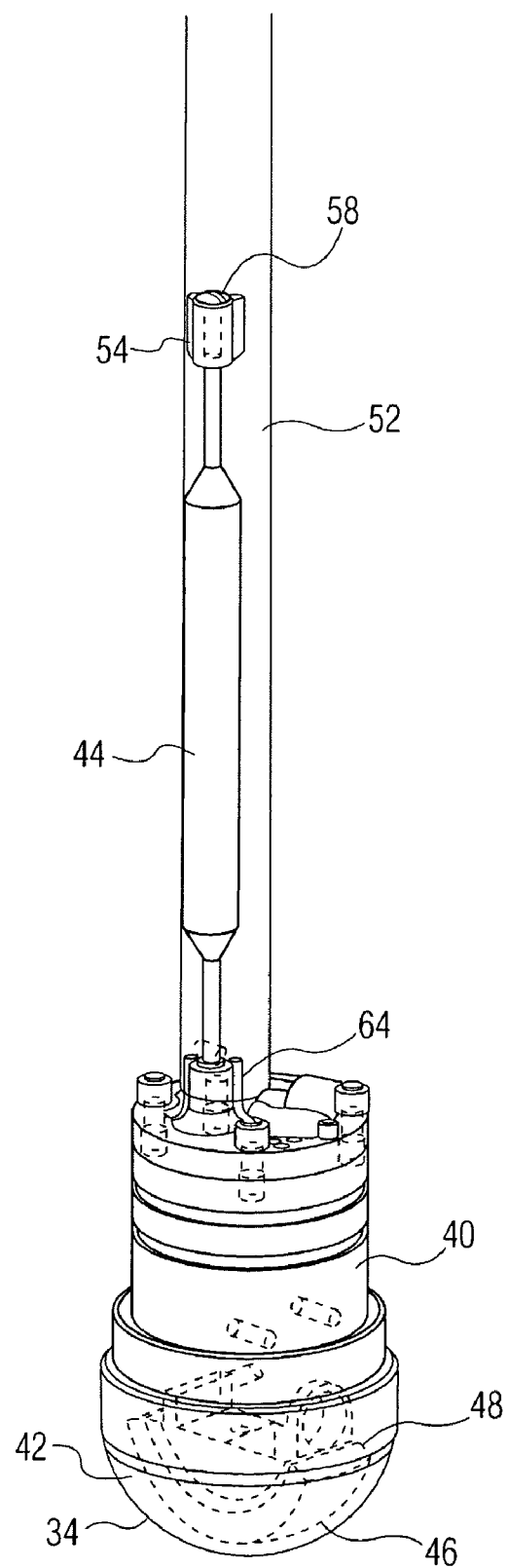
FIG. 3 is a perspective view of the tip assembly of a 3D intracavity probe of the present invention.

Referring now to FIG. 2, an intracavity ultrasound probe 30 for three dimensional imaging which is constructed in accordance with the present invention is shown. The probe 30 includes a handle section 36 by which the user holds the probe for manipulation during use. At the rear of the handle is a strain relief 18 for the probe cable (not shown). Extending from the forward end of the handle 36 is the shaft 32 of the probe which terminates in a dome-shaped acoustic window 34 at the distal end through which ultrasound is transmitted and received during imaging. Contained within the distal end of the shaft is a transducer mount assembly 40 which is also shown in the uncovered view of the tip assembly of FIG. 3. A convex curved array transducer 46 is attached to a transducer cradle 48 at the distal end of the assembly 40. The transducer cradle 48 is pivotally mounted so it can be rocked back and forth in the distal end of the probe and thereby sweep an image plane through a volumetric region in front of the probe. The transducer cradle 48 is rocked by an oscillating drive shaft 50 which extends from a motor and shaft encoder in the handle 36 to the transducer mount assembly 40. The drive shaft extends through an isolation tube 52 in the shaft which serves to isolate the moving drive shaft from the electrical conductors and volume compensation balloon 44 located in the shaft proximal the transducer mount assembly 40. The construction and operation of the rocking mechanism for the transducer cradle 48 is more fully described in concurrently filed U.S. patent application Ser. No. 10/599,306, entitled ULTRASONIC INTRACAVITY PROBE FOR 3D IMAGING, the contents of which are incorporated herein by reference. The echo signals acquired by the transducer array 46 are beamformed, detected, and rendered by the ultrasound system to form a three dimensional image of the volumetric region scanned by the probe.

Because ultrasonic energy does not efficiently pass through air, the array transducer 46 is surrounded by a liquid which is transmissive of ultrasound and closely matches the acoustic impedance of the body which is approximately that of water. The liquid is contained within a fluid chamber 42 inside the transducer mount assembly 40 which also contains the array transducer 46. Water-based, oil-based, and synthetic polymeric liquids may be used. In a constructed embodiment silicone oil is used as the acoustic coupling fluid in the transducer fluid chamber. Further details of the fluid chamber of the embodiment of FIG. 2 may be found in concurrently filed U.S. patent application Ser. No. 10/599,317 entitled ULTRASOUND PROBE WITH MULTIPLE FLUID CHAMBERS, the contents of which are incorporated herein by reference.

Figure 4:
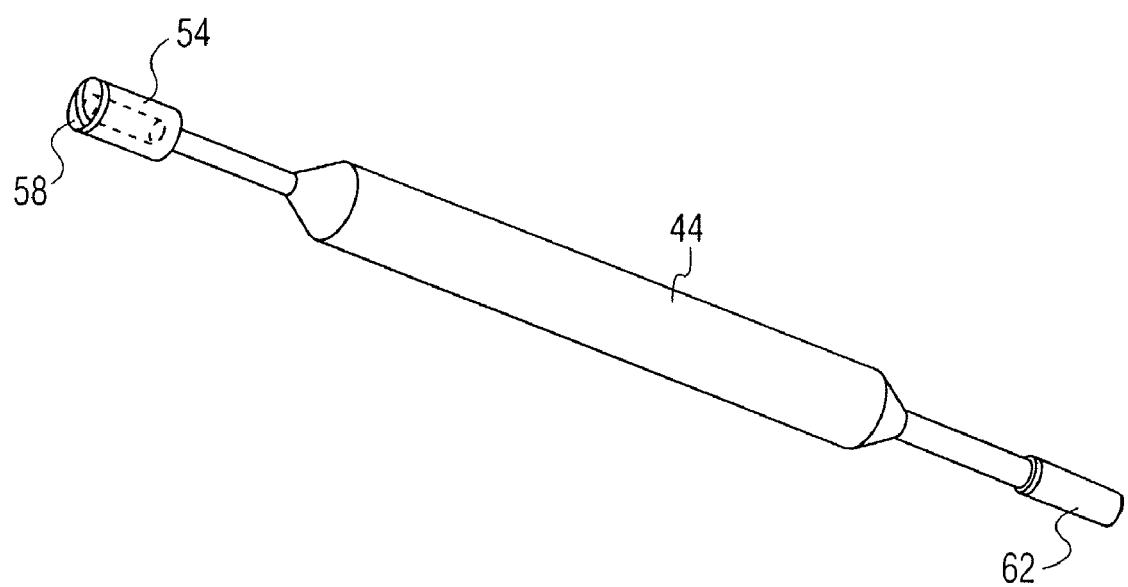
FIG. 4 is a perspective view of a volume compensation balloon constructed in accordance with the principles of the present invention.

In accordance with the principles of the present invention a thin-walled balloon 44 of high performance thermoplastic is coupled to be in fluidic communication with the transducer fluid chamber 42. The balloon is shown in perspective in FIG. 4. In the embodiment of FIG. 4 the balloon 44 is made of a PET polymer which can be made very thin and exhibits a low permeability to fluids such as silicone oil. Silicone oil is a good fluid for probes because it has a low coefficient of expansion $\beta$ with temperature. As a result, the change in volume of the fluid with temperature changes ($\Delta V = \beta V_o \Delta T$) is relatively low. In a constructed embodiment of the present invention the probe was designed to be able to accommodate volume changes $\Delta V$ of the fluid over a temperature range of $-40°$ C. to $+70°$ C. Silicone oil, which is available from Dow Corning Corp. of Midland Mich. was found to exhibit favorable expansion characteristics with coefficients of around $0.00065/°$ C.

In the constructed embodiment in which the balloon 44 was made of a high performance thermoplastic, the balloon wall thickness was approximately 0.6 mil. Wall thicknesses of 5-50 microns (0.0002-0.002 inches) have been found to exhibit the desired compliance ($\Delta P/\Delta V$) while at the same time exhibiting the desired low permeability (p) to fluids. Partially filled balloons of the above wall thickness have been found to offer little resistance to filling and emptying, with compliances of less than 2 psi per ml. The permeability of the high performance thermoplastic material has been found to be an order of magnitude better than typical elastomers, with the permeation rate p per unit thickness generally less than 1.0 and usually in the range of 0.1 to 0.2 $cm^3 \cdot mm/m^2 \cdot day \cdot atm$ (for gas permeability). It should be noted that silicone fluids are known to aggressively permeate many plastics which are impermeable to most other fluids.

The volume compensation balloon should also exhibit good thermal stability. High performance thermoplastics such as PET are used below the glass transition temperature Tg of the material. Elastomeric balloons have a low glass transition temperature, usually in the range of $-10°$ C. to $-80°$ C. and consequently are always highly elastic and rubber-like at their intended operating temperatures, e.g., room temperature. Elastomeric balloons also undesirably have a higher $\Delta P$ vs $\Delta V$ and will become stiff and resist collapsing in colder temperatures. A volume compensation balloon of the present invention should be thermally stable so that the compliance does not deteriorate throughout the intended temperature range of use.

Elastomers, being highly elastic by design, will stretch considerably and can usually be stretched in excess of 100% and still return to the original size and shape. A high performance thermoplastic balloon of the present invention is rigid and can generally only be stretched about 2%-7% before yielding. When excessively stretched the balloon will not return to its original size and shape but will experience plastic deformation. A constructed embodiment exhibited a coefficient of expansion of only $~0.00013/°$ C.

A high performance thermoplastic balloon should also exhibit a high burst strength. A constructed embodiment exhibited a burst strength pressure resistance of 18 atmospheres.

In summary, the factors that should be considered when choosing a balloon material are the ability to fabricate a thin-walled balloon since stiffness of the balloon is principally controlled by wall thickness. The balloon should be rigid yet compliant due to the thin wall design. The material should also exhibit low permeability to the acoustic fluid; good thermal stability so that the balloon will not become stiff at low temperatures; and good integrity in terms of burst strength, tear strength, and puncture resistance.

The fluid chamber 42 in the transducer mount assembly 40 of the embodiment of FIG. 4 has a fluid capacity of 6 ml. The capacity of the volume compensation balloon 44 is chosen in consideration of this fluid volume, and in a constructed embodiment a balloon with a fluid capacity of 0.8 ml was used. The balloon 44 is adhesively attached to a stainless steel fitting 62 at one end of the balloon and to another threaded fitting 54 at the other end. The fitting 62 is then adhesively attached to a port 64 at the proximal end of the transducer mount assembly which connects to the fluid chamber. The fluid is put into the chamber through a fill port also located on the proximal end of the transducer mount assembly 40. The balloon is partially compressed to about half its nominal volume during the filling process. As fluid is applied to the chamber the air in the chamber is forced into the balloon and out the proximal end of the balloon through the threaded fitting 54 until the chamber and the compressed balloon are completely filled with fluid and all of the air in the chamber and balloon has been forced out through the balloon fitting 54. A screw 58 is then screwed into the threaded fitting 54 and the fill port closed. The compression of the balloon is then released. In a constructed embodiment the balloon with a total fluid capacity of 0.8 ml was filled with approximately 0.3 ml of fluid. Should the fluid volume thereafter decrease at lower temperatures fluid from the balloon will flow into the probe fluid chamber with the low stiffness (high compliance) of the balloon allowing this to happen with little resistance, thereby maintaining the fluid pressure substantially constant in the probe. Should the fluid volume increase with increasing temperature, fluid will flow from the fluid chamber into the balloon and the balloon will begin to approach its uncollapsed shape with the ingress of more fluid, again maintaining the pressure within the chamber. The substantially constant pressure of the fluid will thus put no additional stresses on the seals of the fluid chamber. The probe will be able to be transported and used in a wide range of temperatures without the occurrence of leaks or the development of bubbles which would reduce the performance of the probe.

What is claimed is:

1. An ultrasonic probe comprising:
   a transducer located at a distal end of the probe, the transducer being moved within the chamber to scan an image region outside the probe;

a fluid chamber enclosing the transducer within the probe;
an acoustic fluid which is highly transmissive of ultrasound located in the fluid chamber; and
a thin-walled volume compensation balloon formed of a high performance thermoplastic material, and located completely within the probe in fluid communication with the fluid chamber, the volume compensation balloon containing a small fraction of the fluid of the fluid chamber at room temperature.

2. The ultrasonic probe of claim 1, wherein the acoustic fluid comprises a silicone oil.

3. An ultrasonic probe comprising:
a transducer located at a distal end of the probe, the transducer being moved within the chamber to scan an image region outside the probe;
a fluid chamber enclosing the transducer within the probe;
an acoustic fluid which is highly transmissive of ultrasound located in the fluid chamber; and
a thin-walled volume compensation balloon located completely within the probe and formed of a high performance thermoplastic material in fluid communication with the fluid chamber, the volume compensation balloon containing a small fraction of the fluid of the fluid chamber at room temperature,
wherein the thin-walled balloon is formed of a non elastomeric thermoplastic material.

4. The ultrasonic probe of claim 3, wherein the thin-walled balloon exhibits a low permeability to the acoustic fluid.

5. The ultrasonic probe of claim 4, wherein the thin-walled balloon exhibits a high compliance over the designed temperature range of transport and use.

6. The ultrasonic probe of claim 5, wherein the thin-walled balloon exhibit a high thermal stability and is operated at or below the glass transition temperature for the thermoplastic material.

7. An ultrasonic probe comprising:
a transducer located at a distal end of the probe, the transducer being moved within the chamber to scan an image region outside the probe;
a fluid chamber enclosing the transducer within the probe;
an acoustic fluid which is highly transmissive of ultrasound located in the fluid chamber; and
a thin-walled volume compensation balloon located completely within the probe and formed of a high performance thermoplastic material in fluid communication with the fluid chamber, the volume compensation balloon containing a small fraction of the fluid of the fluid chamber at room temperature,
wherein the non elastomeric thermoplastic material comprises a PET polymer.

8. The ultrasonic probe of claim 7, wherein the thin-walled balloon exhibits a high burst strength.

9. An ultrasonic probe comprising:
a transducer located at a distal end of the probe, the transducer being moved within the chamber to scan an image region outside the probe;
a fluid chamber enclosing the transducer within the probe;
an acoustic fluid which is highly transmissive of ultrasound located in the fluid chamber; and
a thin-walled volume compensation balloon located completely within the probe and formed of a high performance thermoplastic material in fluid communication with the fluid chamber, the volume compensation balloon containing a small fraction of the fluid of the fluid chamber at room temperature,
wherein the thin-walled balloon exhibits a high compliance of less than 2 psi per ml; a low permeation rate to acoustic fluid of less than 1.0; a high burst strength in excess of 10 atmospheres; and a thermal stability which does not significantly decrease compliance at low temperatures of operation.

10. An ultrasonic probe for three dimensional imaging comprising:
a probe body enclosing a fluid chamber;
an array transducer movably mounted within the fluid chamber;
a drive mechanism coupled to the array transducer to move the array transducer during scanning;
an acoustic fluid located within the fluid chamber; and
a volume compensation balloon located completely within the probe and in fluidic communication with the fluid chamber, the balloon being formed of a substantially non elastic material and being partially expanded at room temperature.

11. The ultrasonic probe of claim 10, wherein the balloon is approximately half filled with acoustic fluid at room temperature.

12. The ultrasonic probe of claim 11, wherein the balloon contains less than 20% of the fluid of the fluid chamber at room temperature.

13. The ultrasonic probe of claim 10, wherein the balloon is formed of a high performance thermoplastic.

14. The ultrasonic probe of claim 13, wherein the balloon is formed of a PET polymer.

15. The ultrasonic probe of claim 10, wherein the compliance of the wall of the balloon is substantially constant over a design temperature range of transport and use.

16. The ultrasonic probe of claim 15, wherein the design temperature range of use extends below 0°C.

17. The ultrasonic probe of claim 10, wherein the wall thickness of the balloon is less than 1.0 mil, and wherein the wall of the balloon exhibits a low permeability to the acoustic fluid.

18. The ultrasonic probe of claim 10, wherein the probe body comprises a shaft designed for intracavity use of the probe.

* * * * *